(12) United States Patent
Pipenhagen et al.

(10) Patent No.: US 9,913,635 B2
(45) Date of Patent: Mar. 13, 2018

(54) VASCULAR CLOSURE DEVICE HAVING A FLOWABLE SEALING MATERIAL

(71) Applicant: St. Jude Medical Puerto Rico LLC, Caguas, PR (US)

(72) Inventors: Catherine A. Pipenhagen, Plymouth, MN (US); Melissa K. Gardner, Mendota Heights, MN (US); Jyue Boon Lim, New Brighton, MN (US); William R. Fiehler, Chester Springs, PA (US); Gary J. Schorr, St. Paul, MN (US); Janet L. Jacobsen, Maple Grove, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 239 days.

(21) Appl. No.: 14/979,317

(22) Filed: Dec. 22, 2015

(65) Prior Publication Data
US 2016/0113636 A1    Apr. 28, 2016

Related U.S. Application Data

(60) Division of application No. 13/609,115, filed on Sep. 10, 2012, now Pat. No. 9,254,346, which is a (Continued)

(51) Int. Cl.
*A61B 17/08* (2006.01)
*A61B 17/00* (2006.01)
(Continued)

(52) U.S. Cl.
CPC ............ *A61B 17/0057* (2013.01); *A61F 2/00* (2013.01); *A61L 24/00* (2013.01); *A61L 24/0042* (2013.01);
(Continued)

(58) Field of Classification Search
CPC ..... A61B 2017/00672; A61B 17/0057; A61M 25/04; A61L 2400/06; A61L 2400/04; A61L 24/00
See application file for complete search history.

(56) References Cited

U.S. PATENT DOCUMENTS 3,405,083 A    10/1968    Morrison et al.
4,317,445 A    3/1982    Robinson
(Continued)

FOREIGN PATENT DOCUMENTS

WO    0197898 A1    12/2001
WO    2003094749 A1    11/2003
(Continued)

*Primary Examiner* — Gregory Anderson
*Assistant Examiner* — Christina Lauer
(74) *Attorney, Agent, or Firm* — Holland & Hart

(57) ABSTRACT

Various embodiments of a device are shown and disclosed for closing a vascular access puncture site following percutaneous diagnostic or therapeutic interventional procedures. The vascular closure device is configured to safely and accurately deploy a sealing material that undergoes a phase change when deployed inside the tissue tract. The sealing material may be a solid at room temperature and a liquid or gel at body temperature. Also, the sealing material may change from a liquid or gel to a cubic phase when it comes into contact with bodily fluids.

6 Claims, 11 Drawing Sheets

Related U.S. Application Data continuation of application No. 11/968,020, filed on Dec. 31, 2007, now Pat. No. 8,333,787.

(51) Int. Cl.
*A61F 2/00* (2006.01)
*A61L 24/00* (2006.01)
*A61M 25/04* (2006.01)
*A61M 25/02* (2006.01)

(52) U.S. Cl.
CPC ..... *A61M 25/04* (2013.01); *A61B 2017/0065* (2013.01); *A61B 2017/00884* (2013.01); *A61B 2017/00951* (2013.01); *A61L 2400/04* (2013.01); *A61L 2400/06* (2013.01); *A61M 2025/0233* (2013.01)

(56) References Cited

U.S. PATENT DOCUMENTS

| | | |
|---|---|---|
| 4,744,364 A | 5/1988 | Kensey |
| 4,890,612 A | 1/1990 | Kensey |
| 5,021,059 A | 6/1991 | Kensey et al. |
| 5,055,410 A * | 10/1991 | Blumenthal ......... G01N 31/221 422/534 |
| 5,061,274 A | 10/1991 | Kensey |
| 5,108,421 A | 4/1992 | Fowler |
| 5,192,302 A | 3/1993 | Kensey et al. |
| 5,222,974 A | 6/1993 | Kensey et al. |
| 5,282,827 A | 2/1994 | Kensey et al. |
| 5,290,310 A | 3/1994 | Makower et al. |
| 5,292,332 A | 3/1994 | Lee |
| 5,304,184 A | 4/1994 | Hathaway et al. |
| 5,306,254 A | 4/1994 | Nash et al. |
| 5,312,435 A | 5/1994 | Nash et al. |
| 5,320,639 A | 6/1994 | Rudnick |
| 5,342,393 A | 6/1994 | Stack |
| 5,326,350 A | 7/1994 | Li |
| 5,334,216 A | 8/1994 | Vidal et al. |
| 5,352,216 A | 10/1994 | Shiono et al. |
| 5,368,601 A | 11/1994 | Sauer et al. |
| 5,370,660 A | 12/1994 | Weinstein et al. |
| 5,383,896 A | 1/1995 | Gershony et al. |
| 5,383,897 A | 1/1995 | Wholey |
| 5,383,899 A | 1/1995 | Hammerslag |
| RE34,866 E | 2/1995 | Kensey et al. |
| 5,391,183 A | 2/1995 | Janzen et al. |
| 5,403,328 A | 4/1995 | Shallman |
| 5,403,329 A | 4/1995 | Hinchcliffe |
| 5,405,354 A | 4/1995 | Sarrett |
| 5,411,520 A | 5/1995 | Nash et al. |
| 5,417,699 A | 5/1995 | Klein et al. |
| 5,431,639 A | 7/1995 | Shaw |
| 5,431,666 A | 7/1995 | Sauer et al. |
| 5,437,631 A | 8/1995 | Janzen |
| 5,443,481 A | 8/1995 | Lee |
| 5,462,561 A | 10/1995 | Voda |
| 5,486,195 A * | 1/1996 | Myers ................ A61B 17/0057 606/191 |
| 5,496,332 A | 3/1996 | Sierra et al. |
| 5,496,335 A | 3/1996 | Thomason et al. |
| 5,507,744 A | 4/1996 | Tay et al. |
| 5,507,758 A | 4/1996 | Thomason et al. |
| 5,527,322 A | 6/1996 | Klein et al. |
| 5,531,759 A | 7/1996 | Kensey et al. |
| 5,545,178 A | 8/1996 | Kensey et al. |
| 5,549,633 A | 8/1996 | Evans et al. |
| 5,571,181 A | 11/1996 | Li |
| 5,591,205 A | 1/1997 | Fowler |
| 5,593,422 A | 1/1997 | Muijs Van De Moer et al. |
| 5,601,603 A | 2/1997 | Illi |
| 5,613,974 A | 3/1997 | Andreas et al. |
| 5,620,461 A | 4/1997 | Muijs Van De Moer et al. |
| 5,626,601 A | 5/1997 | Gershony et al. |
| 5,643,318 A | 7/1997 | Tsukernik et al. |
| 5,645,566 A | 7/1997 | Brenneman et al. |
| 5,649,959 A | 7/1997 | Hannam et al. |
| 5,653,730 A | 8/1997 | Hammerslag |
| 5,662,681 A | 9/1997 | Nash et al. |
| 5,665,106 A | 9/1997 | Hammerslag |
| 5,674,321 A | 10/1997 | Green et al. |
| 5,676,689 A | 10/1997 | Kensey et al. |
| 5,681,334 A | 10/1997 | Evans et al. |
| 5,700,277 A | 12/1997 | Nash et al. |
| 5,725,498 A | 3/1998 | Janzen et al. |
| 5,725,551 A | 3/1998 | Myers et al. |
| 5,728,122 A | 3/1998 | Leschinsky et al. |
| 5,728,132 A | 3/1998 | Van Tassel et al. |
| 5,728,133 A | 3/1998 | Kontos |
| 5,728,134 A | 3/1998 | Barak |
| 5,741,223 A | 4/1998 | Janzen et al. |
| 5,746,755 A | 5/1998 | Wood et al. |
| 5,755,727 A | 5/1998 | Kontos |
| 5,759,194 A | 6/1998 | Hammerslag |
| 5,766,183 A | 6/1998 | Sauer |
| 5,766,206 A | 6/1998 | Wijkamp et al. |
| 5,782,861 A | 7/1998 | Cragg et al. |
| 5,792,173 A | 8/1998 | Breen et al. |
| 5,807,573 A | 9/1998 | Ljusberg-Wahren et al. |
| 5,810,810 A | 9/1998 | Tay et al. |
| 5,810,846 A | 9/1998 | Virnich et al. |
| 5,810,884 A | 9/1998 | Kim |
| 5,814,065 A | 9/1998 | Diaz |
| 5,820,631 A | 10/1998 | Nobles |
| 5,827,299 A | 10/1998 | Thomason et al. |
| 5,830,130 A | 11/1998 | Janzen et al. |
| 5,843,124 A | 12/1998 | Hammerslag |
| 5,853,421 A | 12/1998 | Leschinsky et al. |
| 5,855,559 A | 1/1999 | Van Tassel et al. |
| 5,855,585 A | 1/1999 | Kontos |
| 5,861,004 A | 1/1999 | Kensey et al. |
| 5,861,005 A | 1/1999 | Kontos |
| 5,868,762 A | 2/1999 | Cragg et al. |
| 5,902,311 A | 5/1999 | Andreas et al. |
| 5,906,631 A | 5/1999 | Imran |
| 5,910,155 A | 6/1999 | Ratcliff et al. |
| 5,919,207 A | 7/1999 | Taheri |
| 5,922,009 A | 7/1999 | Epstein et al. |
| 5,941,897 A | 8/1999 | Myers |
| 5,957,952 A | 9/1999 | Gershony et al. |
| 5,960,990 A | 10/1999 | Nobles et al. |
| 5,964,782 A | 10/1999 | Lafontaine et al. |
| 5,976,161 A | 11/1999 | Kirsch et al. |
| 5,976,411 A | 11/1999 | Feng et al. |
| 5,980,539 A | 11/1999 | Kontos |
| 5,995,502 A | 11/1999 | Fukuda |
| 5,997,555 A | 12/1999 | Kontos |
| 6,007,562 A | 12/1999 | Harren et al. |
| 6,007,563 A | 12/1999 | Nash et al. |
| 6,017,359 A | 1/2000 | Gershony et al. |
| 6,024,747 A | 2/2000 | Kontos |
| 6,033,401 A | 3/2000 | Edwards et al. |
| 6,033,427 A | 3/2000 | Lee |
| 6,036,721 A | 3/2000 | Harren et al. |
| 6,042,601 A | 3/2000 | Smith |
| 6,045,569 A | 4/2000 | Kensey et al. |
| 6,048,357 A | 4/2000 | Kontos |
| 6,048,358 A | 4/2000 | Barak |
| 6,056,768 A | 5/2000 | Cates et al. |
| 6,063,085 A | 5/2000 | Tay et al. |
| 6,071,300 A | 6/2000 | Brenneman et al. |
| 6,077,279 A | 6/2000 | Kontos |
| 6,090,130 A | 7/2000 | Nash et al. |
| 6,110,184 A | 8/2000 | Weadock |
| 6,120,524 A | 9/2000 | Taheri |
| 6,126,675 A | 10/2000 | Shchervinsky et al. |
| 6,136,010 A | 10/2000 | Modesitt et al. |
| 6,139,556 A | 10/2000 | Kontos |
| 6,162,192 A | 12/2000 | Cragg et al. |
| 6,174,322 B1 | 1/2001 | Schneidt |
| 6,183,496 B1 | 2/2001 | Urbanski |
| 6,193,670 B1 | 2/2001 | Van Tassel et al. |
| 6,197,042 B1 | 3/2001 | Ginn et al. |
| 6,206,895 B1 | 3/2001 | Levinson |

(56) References Cited

U.S. PATENT DOCUMENTS

| | | |
|---|---|---|
| 6,228,383 B1 | 5/2001 | Hansen et al. |
| 6,231,561 B1 | 5/2001 | Frazier et al. |
| 6,245,080 B1 | 6/2001 | Levinson |
| 6,398,796 B2 | 6/2002 | Levinson |
| 6,425,911 B1 | 7/2002 | Akerfeldt et al. |
| 6,425,924 B1 | 7/2002 | Rousseau |
| 6,447,513 B1 | 9/2002 | Griggs |
| 6,508,828 B1 | 1/2003 | Akerfeldt et al. |
| 6,547,806 B1 | 4/2003 | Ding |
| 6,569,185 B2 | 5/2003 | Ungs |
| 6,596,012 B2 | 7/2003 | Akerfeldt et al. |
| 6,596,014 B2 | 7/2003 | Levinson et al. |
| 6,682,489 B2 | 1/2004 | Tenerz et al. |
| 6,695,867 B2 | 2/2004 | Ginn et al. |
| 6,712,837 B2 | 3/2004 | Akerfeldt et al. |
| 6,793,938 B2 * | 9/2004 | Sankaram ............ A61K 9/1617 424/422 |
| 6,860,895 B1 | 3/2005 | Akerfeldt et al. |
| 6,890,343 B2 | 5/2005 | Ginn et al. |
| 6,929,655 B2 | 8/2005 | Egnelov et al. |
| 7,331,980 B2 | 2/2008 | Dubrul et al. |
| 7,331,981 B2 | 2/2008 | Cates |
| 7,850,654 B2 | 12/2010 | Belhe et al. |
| 8,012,167 B2 | 9/2011 | Zhu et al. |
| 8,262,693 B2 | 9/2012 | Pai et al. |
| 8,333,787 B2 | 12/2012 | Pipenhagen et al. |
| 8,506,592 B2 | 8/2013 | Killion et al. |
| 2002/0082547 A1 | 6/2002 | Deniega et al. |
| 2003/0171738 A1 | 9/2003 | Konieczynski et al. |
| 2004/0122349 A1 | 6/2004 | Lafontaine et al. |
| 2004/0176800 A1 | 9/2004 | Paraschac et al. |
| 2005/0065549 A1 | 3/2005 | Cates et al. |
| 2005/0085854 A1 | 4/2005 | Ginn |
| 2005/0107750 A1 | 5/2005 | Barongan |
| 2005/0149116 A1 | 7/2005 | Edwards et al. |
| 2005/0149117 A1 | 7/2005 | Khosravi et al. |
| 2005/0228443 A1 | 10/2005 | Yassinzadeh |
| 2006/0264978 A1 | 11/2006 | Belhe et al. |
| 2007/0020228 A1 | 1/2007 | Williams |
| 2007/0021778 A1 | 1/2007 | Carly |
| 2007/0059350 A1 | 3/2007 | Kennedy et al. |
| 2007/0060895 A1 | 3/2007 | Sibbitt et al. |
| 2007/0156084 A1 | 7/2007 | Belhe et al. |
| 2007/0270904 A1 | 11/2007 | Ginn |
| 2009/0054926 A1 | 2/2009 | Pipenhagen et al. |
| 2011/0166595 A1 | 7/2011 | Vidlund et al. |
| 2011/0282383 A1 | 11/2011 | Vidlund et al. |

FOREIGN PATENT DOCUMENTS

| | | |
|---|---|---|
| WO | 2004041122 A2 | 5/2004 |
| WO | 2006065800 A2 | 6/2006 |
| WO | 2007044510 A1 | 4/2007 |

* cited by examiner

VASCULAR CLOSURE DEVICE HAVING A FLOWABLE SEALING MATERIAL

CROSS-REFERENCE TO RELATED PATENT APPLICATIONS

This is a divisional that claims priority to U.S. patent application Ser. No. 13/609,115, filed on 10 Sep. 2012, now issued as U.S. Pat. No. 9,254,346 on 9 Feb. 2016, which is a continuation of U.S. patent application Ser. No. 11/968,020, filed on 31 Dec. 2007, now issued as U.S. Pat. No. 8,333,787 on 18 Dec. 2012, the disclosure of which is incorporated in its entirety by this reference. U.S. patent application Ser. No. 11/842,509, filed on 21 Aug. 2007, now issued as U.S. Pat. No. 8,568,445 on 29 Oct. 2013, is hereby incorporated by reference herein in its entirety. In the event of a conflict, the subject matter explicitly recited or shown herein controls over any subject matter incorporated by reference. All definitions of a term (express or implied) contained in any of the subject matter incorporated by reference herein are hereby disclaimed. The paragraphs shortly before the claims dictate the meaning to be given to any term explicitly recited herein subject to the disclaimer in the preceding sentence.

BACKGROUND

Catheter based diagnostic and interventional procedures such as angiograms, balloon angioplasty, stenting, atherectomy, thrombectomy, device placement, etc. are commonly employed to treat patients with vascular obstructions or other abnormalities accessible through the vasculature of the human body. Such interventions are less traumatic to the body than previous surgical interventions and therefore are growing in use.

To gain access to the vasculature, the Seldinger technique is commonly employed. This involves placing a small gauge hollow needle through the skin at about a 30 degree angle to intersect the desired vessel, commonly, but not always, the femoral artery in the groin area. The needle is known to have punctured the vessel wall when blood exits the needle at the proximal end. A guidewire is inserted through the needle into the vessel and the needle is removed. A dilator with a lumen sized to fit the guidewire has a leading tapered end and an outside diameter sized to fit closely in an introducer sheath placed over it. The introducer sheath size is selected (typically 5-8 Fr) to accommodate the catheters anticipated to be used in the procedure. The introducer sheath and tapered dilator are advanced together over the guidewire through the skin and into the vessel. The dilator and guidewire are then removed, since the vascular pathway from outside the body through the sheath and into the vessel has been established. A self sealing stretchable valve at the proximal end of the introducer sheath minimizes blood loss from the introducer sheath during the procedure.

Following the procedure and after all of the catheters and guidewires have been removed from the body, the introducer sheath is removed from the artery. Historically, this has been done by exerting manual pressure on the vessel upstream from the access site to lower blood pressure while the introducer sheath was removed. Once removed, manual pressure is applied directly to the skin above the access puncture for about thirty minutes to inhibit blood loss until the body's natural clotting process sealed the puncture. This technique is generally considered unsatisfactory because it is uncomfortable for the patient and requires a significant amount of nursing staff time.

Sealing the artery by manual compression is rapidly being replaced by medical devices designed to provide a vascular puncture seal in less than five minutes. These devices are intended to be effective and easy to use by medical personnel. The devices range from mechanical suturing devices to collagen plugs, vascular clips, staples, and use of adhesives and sealants. These various approaches have had varying degrees of success and ease of use.

One of the more commonly used devices for closing vessel punctures achieves hemostasis at the vessel puncture site by closing the puncture with an absorbable intra-vessel (e.g., intra-arterial) anchor and an extra-vessel (e.g., extra-arterial) collagen sponge. The anchor and collagen are held together with a self tightening suture loop and slip knot, which, when tightened, sandwiches the puncture hole between the anchor and the collagen sponge. The device is easy to use and the bio-absorbable anchor, collagen, and suture sandwich seals the vessel quickly, is more comfortable for the patient, saves valuable nurse time, and allows early patient ambulation.

Although such collagen devices can be highly effective, a substantial number of punctures in, for example, the femoral artery, may cause the patient to be ineligible to use such a device. Factors that may prevent use of this device include presence of peripheral vascular disease, poor needle stick location (too high or too low), or small vessel size which interferes with anchor placement and prevents proper seating of the anchor against the arterial wall.

In an effort to overcome some of these problems, vascular closure devices have been developed that deposit a plug outside the vessel with no component inside the vessel. Such devices may generally require, however, consistently placing the plug near the arterial wall. Unfortunately, these devices suffer from a number of drawbacks. For example, the pressure exerted on the plug as the heart beats can cause the plug to move away from the hole in the vessel resulting in a hematoma or other complication at the puncture site. Also, the plug may not seal the puncture tract/hole in the blood vessel sufficiently to prevent leakage.

Accordingly, it would be desirable to provide an improved vascular closure device or vascular sealing device that is easy to use, seals quickly and securely, and leaves no component in the blood vessel. A number of embodiments of such improved vascular closure devices are shown and described herein.

SUMMARY

Various embodiments of vascular closure devices are shown and described herein. The vascular closure devices are, generally speaking, hemostatic devices intended to stop bleeding by closing vascular access puncture sites following percutaneous diagnostic or therapeutic procedures. It should be appreciated that the vascular closure devices shown and described herein may be used to close any puncture in any blood vessel although the vascular closure devices are most commonly used to close arteriotomies. It should also be appreciated that the closure devices may be used to close punctures or holes in other bodily vessels.

One embodiment of the vascular closure device may include a vessel locating member configured to be inserted through a hole in a blood vessel to locate a wall of the blood vessel that is adjacent to the hole and sealing material configured to be deployed adjacent to the hole and outside of the blood vessel. The sealing material may be configured to undergo a phase change when deployed to close the hole in the blood vessel. In one embodiment, the sealing material may comprise a monoglyceride including a fatty acid group having 12 to 22 carbon atoms. In another embodiment, the sealing material may have a melting point that is no more than 37° C. In yet another embodiment, the sealing material may have a melting point of about 27° C. to 37° C., about 30° C. to 37° C., or about 34° C. to 37° C. The sealing material may change to a cubic phase when deployed to close the hole in the blood vessel.

Another embodiment of a vascular closure device may include sealing material configured to flow out of the vascular closure device and into a tissue tract to close the hole in the blood vessel. The vascular closure device may be configured so that the sealing material flows out of the vascular closure device in a direction that is not parallel to the tissue tract. In one embodiment, the vascular closure device may be configured so that the sealing material flows out of the vascular closure device in a direction that is at least substantially perpendicular to the tissue tract. In another embodiment, the vascular closure device may include a perforated tube that is configured to dispense the sealing material into the tissue tract. The perforated tube may have a distal end that is blocked to prevent the sealing material from flowing out of the perforated tube in a direction that is parallel to the tissue tract. The perforated tube may also include a plurality of holes which are of different sizes to control the amount of sealing material dispensed at different points along the length of the perforated tube. In one embodiment, the size of the plurality of holes may increase nearer the distal end of the perforated tube.

Another embodiment of a vascular closure device may include a carrier tube and sealing material positioned in the carrier tube. The sealing material may be configured to be deployed in the tissue tract to close the hole in the blood vessel by retracting the carrier tube to expose the sealing material to the tissue tract. In one embodiment, the vascular closure device may include a stopper positioned between the carrier tube and the sealing material to prevent the sealing material from moving proximally when the carrier tube is retracted.

Another embodiment of a vascular closure device may include a vessel locating member which is configured to locate the wall of the blood vessel that is adjacent to a hole in the blood vessel and which includes a plurality of structural support members covered by a resilient material. The vessel locating member may be configured to move between an expanded configuration to allow the vessel locating member to contact the interior surface of the wall of the blood vessel and a contracted configuration to allow the vessel locating member to pass through the hole in the blood vessel. In one embodiment, the vessel locating member may include a tube having a wall with a plurality of cuts in it that form the structural support members. The wall of the tube may be configured to expand where the structural support members are located when the tube is compressed. The vessel locating member may be formed by a nitinol tube. The resilient material may include isoprene. The resilient material may be provided to create a seal with the interior surface of the wall of the blood vessel and thereby prevent the sealing material from entering the blood stream.

One embodiment of a method of closing the hole in the blood vessel may include locating the wall of the blood vessel adjacent to the hole and deploying sealing material in the tissue tract to close the hole in the blood vessel. The sealing material may be deployed a predetermined distance from the wall.

Another embodiment of a method of closing the hole in the blood vessel may include deploying sealing material in the tissue tract to close the hole in the blood vessel so that the sealing material flows out of the vascular closure device in a direction that is not parallel to the tissue tract. In one embodiment, the sealing material may flow out of the vascular closure device in a direction that is at least substantially perpendicular to the tissue tract. In another embodiment, the sealing material may flow through a perforated tube and out into the tissue tract. The perforated tube may include a plurality of holes having different sizes to control the amount of sealing material dispensed at different points along the length of the perforated tube. In one embodiment, the size of the plurality of holes may increase nearer the distal end of the perforated tube. The sealing material may have a distal end that is blocked to prevent the sealing material from flowing out of the perforated tube in a direction that is parallel to the tissue tract to prevent the sealing material from passing through the hole in the blood vessel and into the blood stream.

Another embodiment of a method of closing the hole in the blood vessel may include inserting the vascular closure device into the tissue tract and retracting the carrier tube to expose the sealing material to the tissue tract thereby enabling the sealing material to flow into the tissue tract. In one embodiment, the vascular closure device may include a stopper positioned between the carrier tube and the sealing material to prevent the sealing material from moving proximally when the carrier tube is retracted.

Another embodiment of a method of closing the hole in the blood vessel may include inserting one embodiment of the vessel locating member that includes a plurality of structural support members covered by a resilient material through the hole and into the blood vessel, expanding the vessel locating member, and moving the vessel locating member into contact with the wall of the blood vessel.

The foregoing and other features, utilities, and advantages of the subject matter described herein will be apparent from the following more particular description of certain embodiments as illustrated in the accompanying drawings.

DRAWINGS

DETAILED DESCRIPTION

Figure 1:
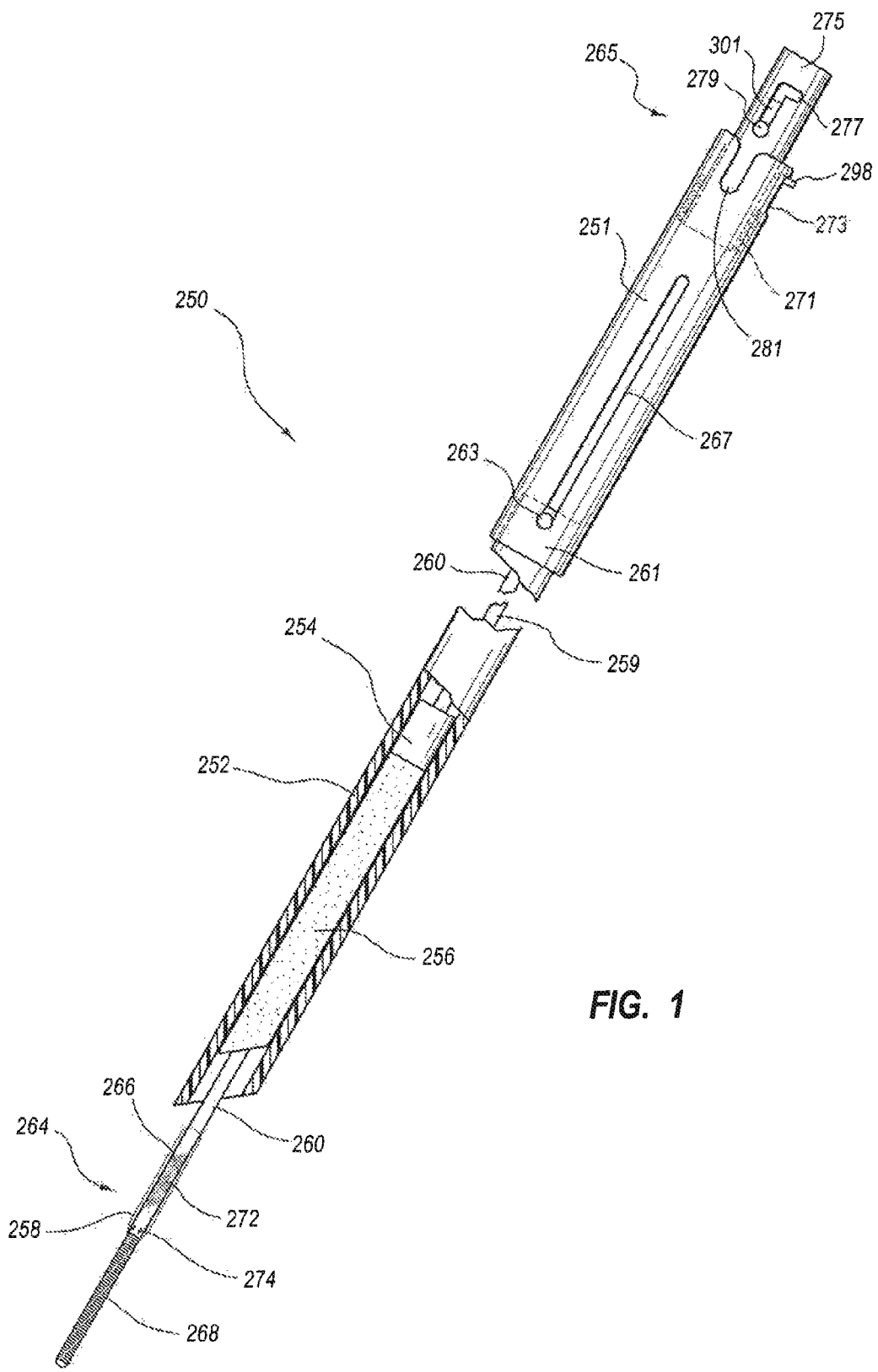
FIG. 1 shows a side view of one embodiment of a vascular closure device.

A number of embodiments of vascular closure devices are shown and described herein. The vascular closure devices may be used to close a hole or puncture in a blood vessel such as an arteriotomy. The vascular closure devices are hemostatic devices that may be used to stop bleeding from vascular puncture sites following percutaneous diagnostic or therapeutic procedures.

The vascular closure devices may be used to deploy sealing material adjacent to and outside of the hole in the blood vessel. The sealing material functions to block the hole in the blood vessel and/or the tissue tract to stop the bleeding. In one embodiment, the sealing material may be a lipid based sealing material. For example, the sealing material may include monoglycerides of saturated and unsaturated fatty acids. The sealing material may include one or more of such monoglycerides alone or in combination with other materials such as therapeutic agents, additives, and carrier materials. The therapeutic agents may include drugs or other substances that provide local or systemic therapeutic effect in the body. Additives may be included to alter the physical properties such as the melting point, strength, resiliency, etc. of the sealing material.

It should be appreciated that there are a wide number of substances, mixtures, molecules, etc. that may be used as the sealing material. In one embodiment, the sealing material may comprise a monoglyceride including a fatty acid group having 12 to 22 carbon atoms. In another embodiment, the sealing material may include glycerol monooleate, glycerol monostearate, glycerol monopalmitate, glycerol monolaurate, glycerol monocaproate, glycerol monocaprylate, glycerol monolinoleate, glycerol monolinolenate, glycerol monomyristate, and/or glycerol monoarachidonate. Those materials that may be preferable for use as the sealing material include glycerol, mono oleate, glycerol monolinoleate, and/or glycerol monolinolenate, in any combination or amount.

The sealing material may melt, gel, or otherwise undergo a phase change when deployed adjacent to the hole in the blood vessel. In order for the sealing material to melt, it is desirable for the sealing material to have a melting point that is less than bodily temperature but high enough that the sealing material is a solid at room temperature. After the sealing material has been inserted into the tissue tract, it is heated by the patient's body until it begins to melt or gel. In one embodiment, the sealing material may have a melting point that is no more than 37° C. In another embodiment, the sealing material may have a melting point that is about 27° C. to 37° C., about 30° C. to 37° C., or about 34° C. to 37° C.

Once the sealing material has melted, it may flow into the tissue tract toward the hole in the blood vessel. At the same time, the sealing material may begin to expand and form a cubic phase due to exposure to bodily fluids. In one embodiment, the sealing material may expand up to 46% of its original size. The sealing material may also exhibit adhesive properties that help to hold the sealing material in place in the tissue tract. The expansion of the sealing material and formation of the cubic phase (the sealing material becomes solid or non-flowable in the cubic phase) may act to hold the sealing material in place over the hole in the blood vessel thereby closing the hole in the blood vessel.

A number of vascular closure devices are described herein that facilitate deployment of the sealing material in the tissue tract of the patient. The sealing material blocks the tissue tract and stops the bleeding. In one embodiment, the sealing material is bio-absorbable to allow it to be removed by the body's natural processes. In another embodiment, the sealing material may be deployed with and coupled to another bio-absorbable component such as a sealing plug (e.g., collagen plug) or anchor both of which may also be bio-absorbable (e.g., PLA and PGA materials). In one embodiment, the vascular closure devices may be configured to not leave any components inside the blood vessel after the closure procedure is over (i.e., an extra-vascular closure device). In this embodiment, the sealing material and any other components left in the patient are outside of the blood vessel.

The success of an extra-vascular closure device depends on a number of factors. One factor that significantly impacts the ability of the vascular closure device to properly seal the hole in the blood vessel is the proper placement of the sealing material and/or other components relative to the hole. If these components are improperly positioned (e.g., too far away from the hole), a hematoma or other complication may arise.

Before describing the particular embodiments of the vascular closure devices, it should be appreciated that the features, advantages, characteristics, etc. described or shown in connection with one of the embodiments may be applied to or combined with any other embodiment to form an additional embodiment unless noted otherwise. This also applies to those embodiments that are incorporated herein by reference. Thus, the various embodiments may be modified in a variety of ways to produce many additional embodiments.

Figure 2:
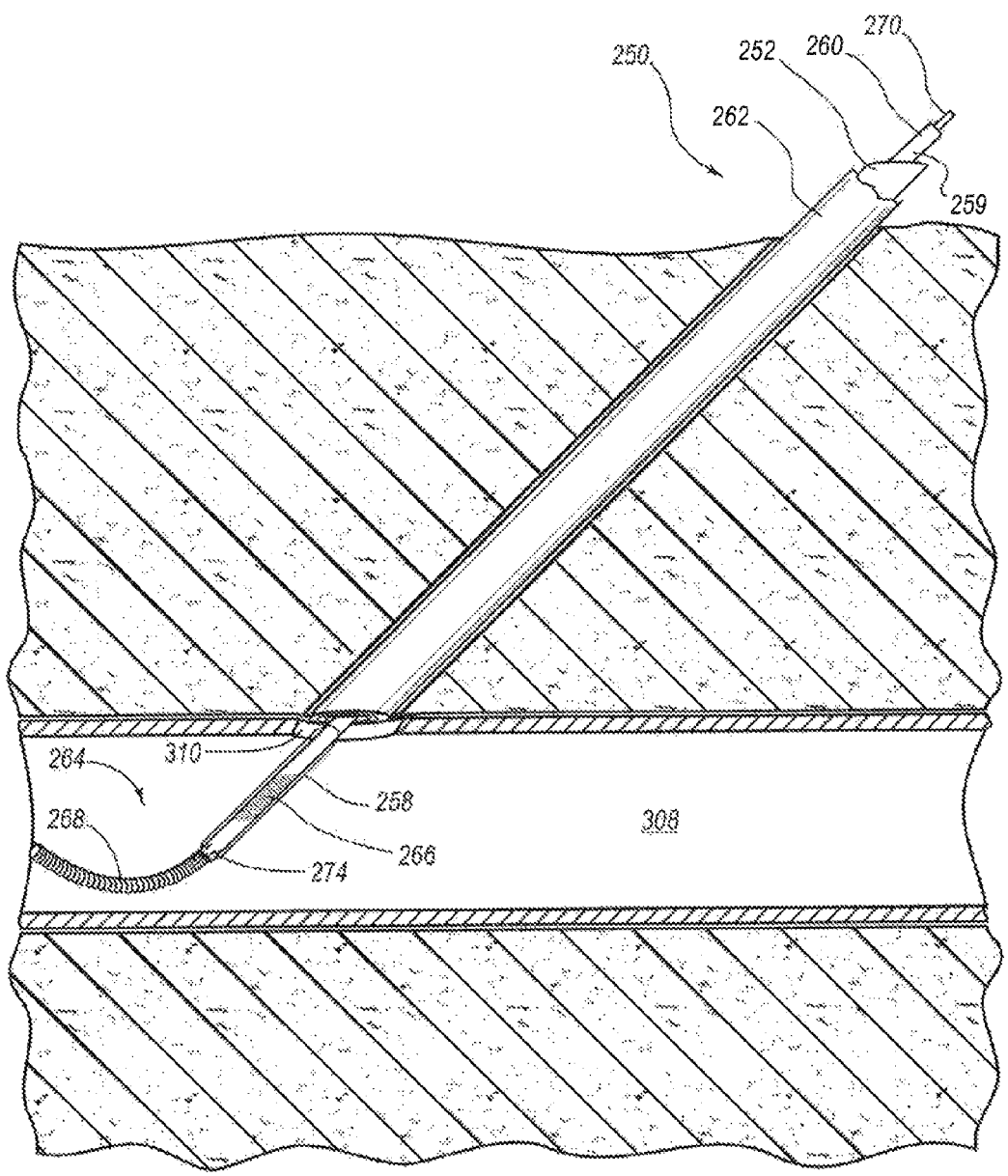
FIG. 2 shows the vascular closure device inserted into a blood vessel.

Referring to FIG. 1, one embodiment of a vascular closure device 250 is shown that may be used to close and/or seal a hole or puncture in a blood vessel such as an arteriotomy. The vascular closure device 250 has a distal end 264 and a proximal end 265 and includes a handle 251, a carrier tube or carrier member 252, sealing material 256, a stopper 254, and a vessel locator assembly or vessel locator portion 260. The vessel locator assembly 260 includes a central tube 259 that extends through the handle 251, the carrier tube 252, the stopper 254, and the sealing material 256. The vessel locator assembly 260 also includes a vessel locating member 266, which is covered by a membrane or covering 258, a spring 268, and a core wire or guide wire 270 (FIG. 2).

The handle 251 is positioned at the proximal end 265 of the vascular closure device 250 and allows the user to manipulate the various components of the device 250 to facilitate closing the hole in the blood vessel. In the embodiment shown in FIG. 1, the handle 251 includes a first tube 261 having a distal end that is sized to slidably receive the carrier tube 252 and a proximal end that is sized to slidably receive a second tube 275. The first tube 261 includes a slot 267 that receives an actuation member, protrusion, or pin 263 that extends outward from the carrier tube 252. The user can reciprocally move the actuation member 263 proximally and distally in the slot 267 to retract and extend, respectively, the carrier tube 252. Retracting the carrier tube 252 when the vascular closure device 250 is deployed exposes the sealing material 256 to the tissue tract.

Returning to the vessel locator assembly 260, the core wire or guide wire 270 (FIG. 2) extends from the proximal end 265 to the distal end 264 of the vascular closure device 250 inside the central tube 259. The spring 268 (e.g., coiled stainless steel spring) is coupled to the distal end of the central tube 259 and surrounds the core wire 270. The spring 268 may be coupled to the central tube 259 using any suitable fastening mechanism or technique such as, for example, brazing, soldering, or epoxy adhesive. The distal end of the core wire 270 where it travels through the spring 268 is tapered or reduced in diameter to make the distal end 264 of the vascular closure device 250 more flexible. The distal end of the core wire 270 is coupled to the distal end of the spring 268. Both the core wire 270 and the spring 268 are configured to be atraumatic to prevent the distal end 264 of the vascular closure device 250 from puncturing or damaging the blood vessel.

The vessel locating member 266 is positioned at the distal end of the vessel locator assembly 260 and is covered by the membrane 258. The vascular closure device 250 is configured so that when it is inserted into the puncture tract, the vessel locating member 266 is positioned inside the blood vessel. The vessel locating member 266 may be configured to move between the contracted configuration shown in FIG. 1 and the expanded configuration shown in FIG. 3. This allows the vessel locating member 266 to be inserted into the blood vessel, expanded, and then moved into contact with the interior wall of the blood vessel adjacent to the hole. The vessel locating member 266 and the sealing material 256 are spaced apart a predetermined distance so that when the vessel locating member 266 is positioned against the interior wall of the blood vessel, the sealing material 256 is positioned just outside of the hole in the blood vessel. In the embodiment shown in the FIGS, the vessel locating member 266 includes a plurality of strut members or structural support members 272 formed by making a series of cuts around the vessel locator assembly 260 in a spiral pattern. The cuts may be made using a laser or any other suitable device or technique.

The vessel locating member 266 moves between the expanded configuration and the contracted configuration as follows. The core wire 270 is coupled to the central tube 259 at a position 274 that is distal to the vessel locating member 266. The vessel locating member 266 may be expanded by moving the core wire 270 proximally. Proximal movement of the core wire 270 exerts a compressive force on the central tube 259 that causes the strut members 272 to deflect outwardly. In one embodiment, the strut members 272 bow and twist as they deflect outwardly. The result, shown in FIG. 3, is that the strut members 272 form a plurality of petal shaped vessel locators that extend radially outward from the central tube 259.

The vessel locating member 266 may be moved back to the contracted configuration shown in FIG. 1 by moving the core wire 270 in a distal direction to its original position. Distal movement of the core wire 270 exerts a tension force on the central tube 259 that causes the strut members 272 to straighten and contract or collapse so that the strut members 272 are again in line with the remainder of the central tube 259.

As shown in FIG. 1, the core wire 270 may be coupled to the handle 251 of the vascular closure device 250 in a way that allows the core wire 270 to be moved back and forth as explained. In this embodiment, the core wire is coupled to a plunger 301 positioned inside the second tube 275. An actuation member 79 extends outward from the plunger 301 and travels in a slot 277 in the second tube 275. The user can move the plunger 301, and consequently the core wire 270, proximally and distally with the actuation member 279. The actuation member 279 can be moved laterally in the slot 277 to lock the core wire 279 in the proximal position.

Figure 3:
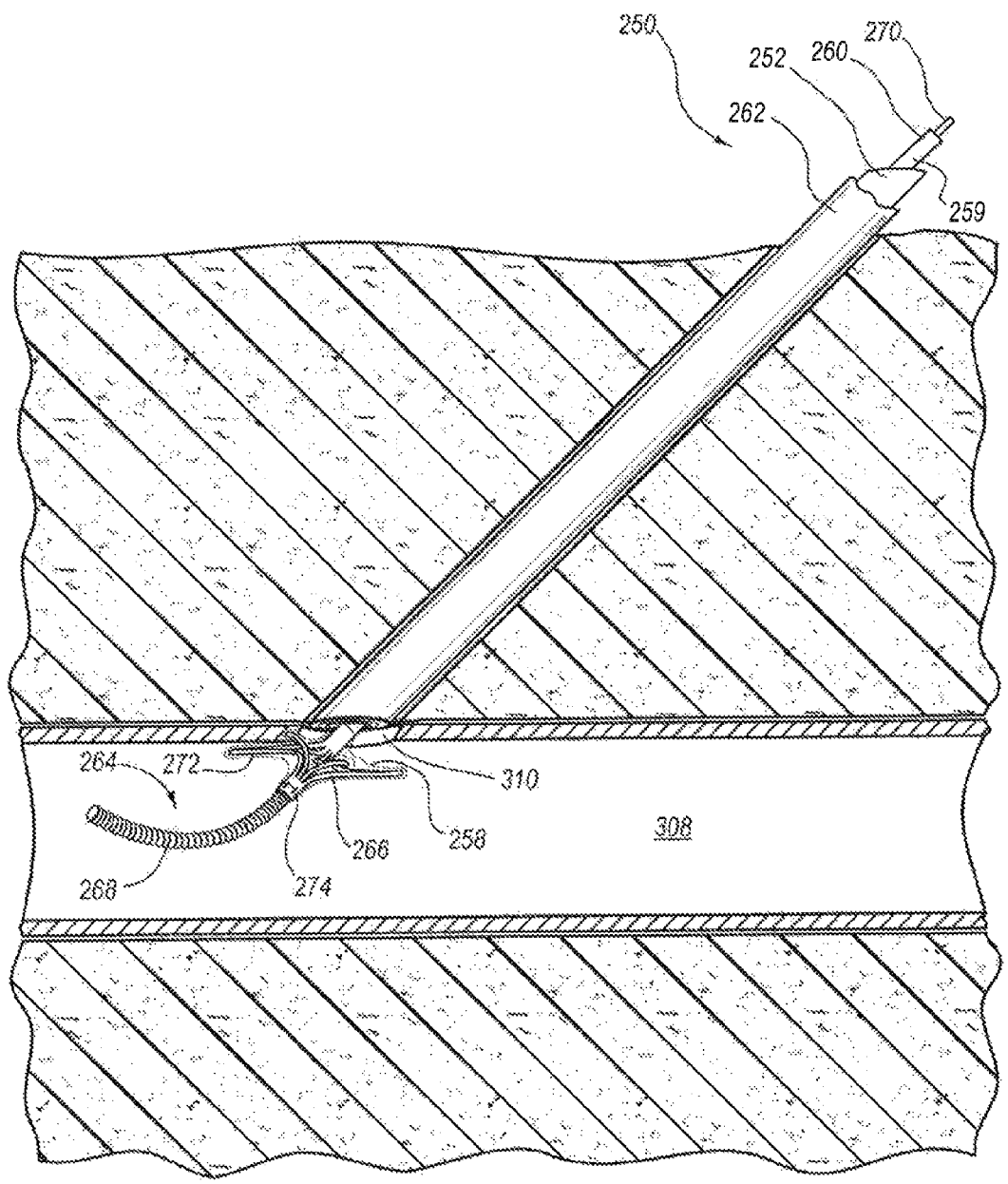
FIG. 3 shows the vascular closure device inserted into the blood vessel with a vessel locating member in an expanded position and spaced apart from the interior wall of the blood vessel.

The cuts in the wall of the central tube 259 may be configured so that the strut members 272 of the vessel locating member 266 form a plane that is not perpendicular to the vessel locator assembly 260 as shown in FIG. 3. This may be desirable to create more uniform contact between the vessel locating member 266 and the interior wall of the blood vessel. Since the puncture tract is usually at a 20-45 degree angle relative to the blood vessel, the plane formed by the vessel locating member 266 may also be at an approximately 20-45 degree angle relative to a lengthwise axis of the vessel locator assembly 260. When the vessel locating member 266 is in the blood vessel, the vessel locating member 266 may be roughly parallel to the interior wall of the blood vessel just before the vessel locating member 266 contacts the interior wall.

It should be appreciated that the configuration of the vessel locating member 266 can be modified in any of a number of ways. For example, the vessel locating member 266 may be configured to be perpendicular to the lengthwise axis of the vessel locator assembly 260. In another embodiment, the vessel locating member 266 may include an inflatable balloon (e.g., inflated with a fluid such as saline solution, carbon dioxide, etc., dispensed from a syringe or other device or container).

It should be appreciated that the central tube 259 and any of the other components of the vessel locator assembly 260 may be made of any suitable material such as metal, plastics, or composites. Since the vascular closure device 250 is a medical device, the materials used may also be medical grade (medical grade metals, plastics, or composites). In one embodiment, the central tube 259 and the core wire 270 may be made of metals such as stainless steel or memory shape metals such as nitinol, and the like. In another embodiment, the central tube 259 may be made of a memory shape material such as nitinol (e.g., nitinol hypotube) to allow the vessel locating member 266 to repeatedly expand and contract. In yet another embodiment, the core wire 270 may be a stainless steel wire.

The stopper 254 is provided to prevent the sealing material 256 from moving proximally as the carrier tube 252 moves proximally. Accordingly, the stopper 254 is positioned just proximal to the scaling material 256 inside the carrier tube 252 and the stopper 254 is coupled to the central tube 259 so that it is fixed in position.

Referring to FIG. 1, the vascular closure device 250 may be configured to indicate when the vessel locating member 266 is in contact with the interior wall of the blood vessel. One problem associated with locating the wall of the blood vessel is that the user may be unable to feel when the vessel locating member 266 has contacted the wall of the blood vessel. The user may continue to pull on the vascular closure device 250 causing it to distort and bend until it passes through the hole in the blood vessel or the expanded vessel locating member 266 may tear through the hole in the wall of the blood vessel causing additional injury to the patient.

The first tube 261 and the second tube 275 are coupled together in a manner that signals to the user when the expanded vessel locating member 92 is positioned against the interior wall of the blood vessel. The second tube 275 is positioned to move lengthwise in the first tube 261. The core wire 270 is coupled to the plunger 301 which is in the second tube 275. When the vessel locating member 266 contacts the interior wall of the blood vessel, the tension on the core wire 270 pulls the second tube 275 further into the first tube 261. A spring 271 is positioned between the first tube 261 and the second tube 275 to bias the second tube 275 in the proximal direction and resistant the tension exerted by the core wire 270. The spring 271 is configured to provide just the right amount of force so that the spring 271 is only compressed when the vessel locating member 266 has contacted the interior wall of the blood vessel.

An indicator pin 298 extends outward from the second tube 275 and travels in a slot 273 in the first tube 261. The indicator pin 298 prevents the spring 271 from biasing the second tube 275 out the proximal end of the first tube 261. As the spring 271 is compressed, the indicator pin 298 moves distally in the slot 273. In operation, the user can pull back on the vascular closure device 250 while watching the indicator pin 298. When the indicator pin 298 begins to move distally in the slot 273, the user knows that the vessel locating member 266 is positioned against the interior wall of the blood vessel.

It should be appreciated that numerous other methods may be used to signal the user that the vessel locating member 266 is positioned against the interior wall of the blood vessel. The signal may be visual, auditory, or any other suitable type of signal. In one embodiment, the vascular closure device 250 may be configured to emit a beep to alert the user that the vessel locating member 266 is positioned against the interior wall of the blood vessel.

It should be appreciated that the design of the vascular closure devices 250 may be altered in any of a number of ways. For example, FIGS. 8-11 show another embodiment of the vascular closure device 250. In this embodiment, the vascular closure device 250 includes a perforated tube 292 that is used to dispense the sealing material 256 into the tissue tract. In one embodiment, the vascular closure device 250 may be provided with a syringe coupled to the proximal end of the perforated tube 292. The syringe may be used to inject the sealing material 256 out through the holes 293 in the perforated tube 292. The distal end of the perforated tube 292 may be blocked or closed so that the sealing material 256 is forced out the sides of the perforated tube 292 creating a lateral dispersion against the walls of the tissue tract instead of down against the hole, which may result in sealing material entering the blood stream.

Figure 9:
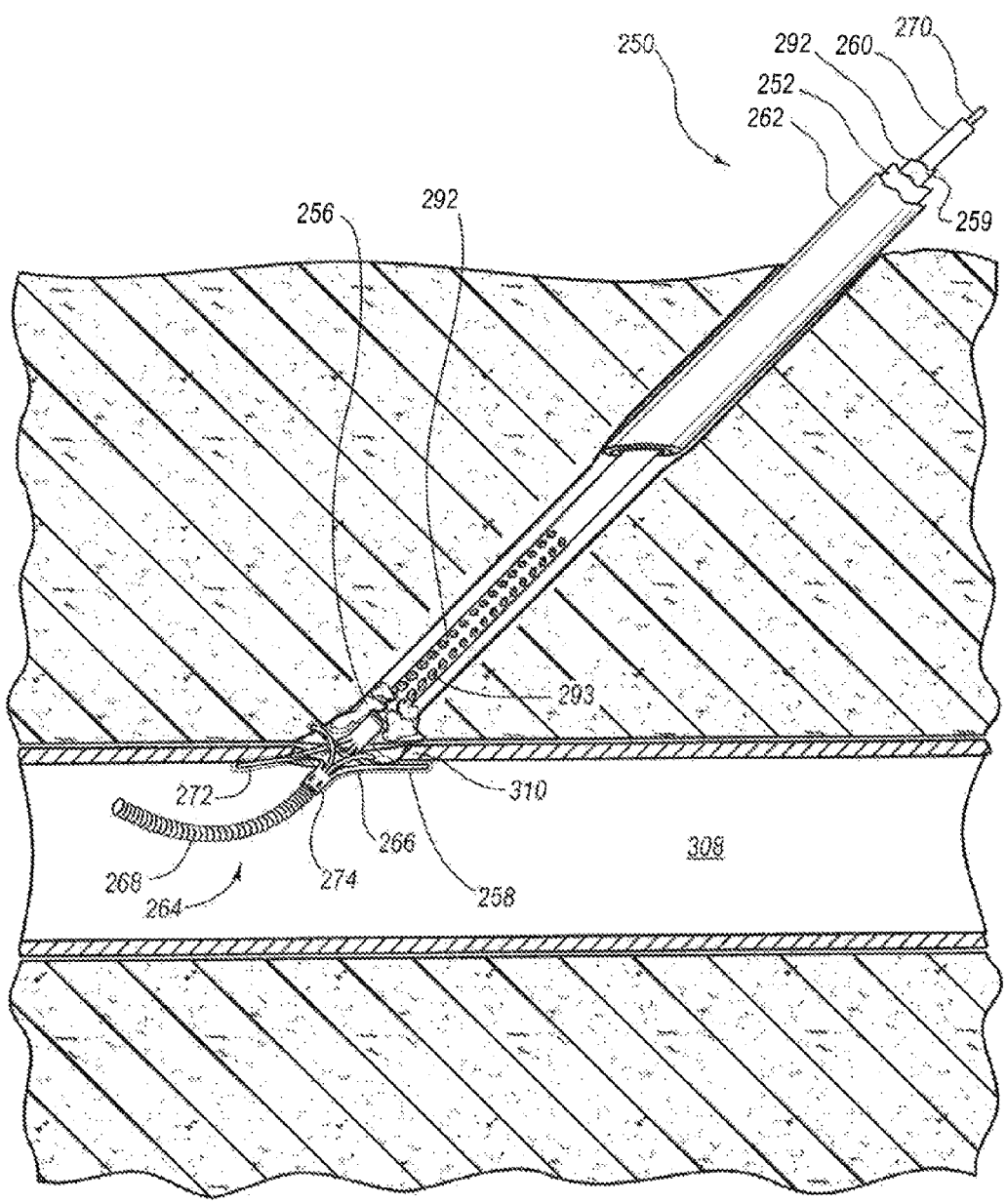
Figure 10:
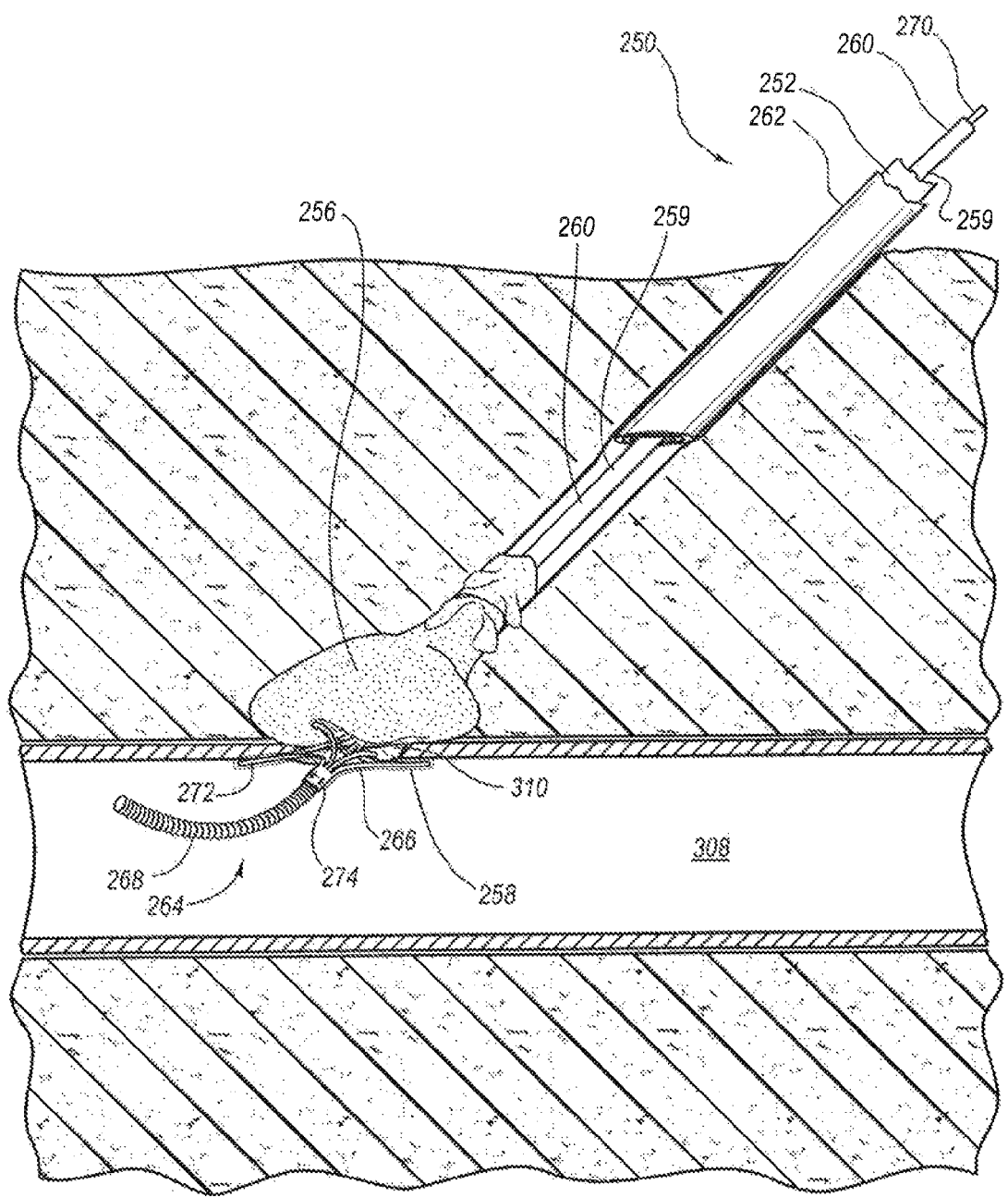
Figure 11:
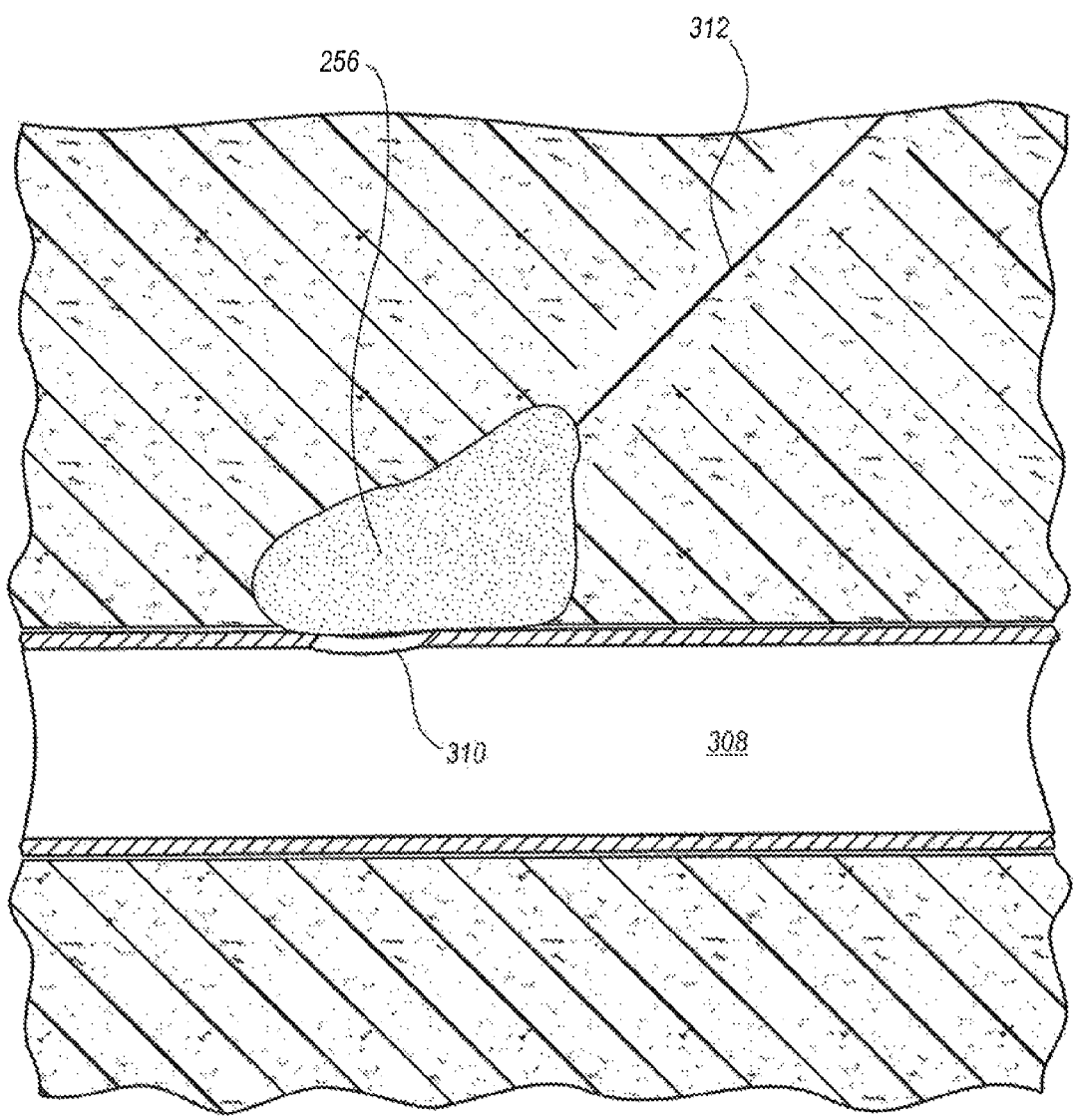

As shown in FIG. 9, the holes 293 in the perforated tube 292 may be sized to regulate the flow of the sealing material 256. For example, the holes 293 may get larger moving in a distal direction along the perforated tube 292 so that the largest holes 293 are positioned nearest the distal end of the perforated tube 292. This configuration results in an even amount of sealing material 256 being dispensed along the perforated tube 292. It should be appreciated that in other embodiments, the holes 293 may be configured to be the same size or all of the holes 293 may be unique sizes. Numerous configurations are possible.

The vascular closure devices 250 may also have numerous other configurations as well. For example, any of the embodiments of vascular closure devices shown in the materials incorporated by reference in the first paragraph of this specification may be modified using the principles described herein to use the sealing material 256.

A method of closing a hole 310 in a blood vessel 308 using the vascular closure device 250 is described in connection with FIGS. 2-11. Once the procedure is over and the user is ready to close the hole in the blood vessel, the initial step may be to exchange the procedural access sheath for the closure sheath 262. This is done by placing a guidewire through the procedural sheath and into the blood vessel 308. The procedural sheath is then withdrawn from the body while holding digital pressure on the blood vessel 308, upstream from the sheath, and while holding the guidewire in place. Next, a closure dilator is placed within the closure sheath 262 and the distal tapered end of the closure dilator is back-loaded onto the guidewire. The closure dilator and the closure sheath 262 are advanced together distally over the guidewire, through the tissue tract 312, and into the blood vessel 308.

In one embodiment, the closure sheath 262 includes a distal side hole (not shown) near the distal end of the closure sheath 262. The closure dilator also includes a distal side hole that is configured to align with the distal side hole in the closure sheath 262 when the closure dilator is positioned in the closure sheath 262. The closure dilator also has a proximal side hole at the proximal end of the closure dilator that is in fluid communication with the distal side hole of the closure dilator and the closure sheath. In one embodiment, the distal and proximal side holes may be fluidly connected by way of a dedicated lumen or bore. In another embodiment, the distal and proximal side holes may be fluidly connected by the central lumen of the closure dilator that the guidewire is positioned in.

The distal and proximal side holes in the closure sheath 262 and the closure dilator are provided to allow blood to flash back when the closure sheath 262 is correctly positioned in the blood vessel 308. Once blood flows out the proximal side hole of the closure dilator, the user pulls the closure sheath 262 in a proximal direction until the blood flow just stops. The closure sheath 262 is now placed in the correct position to continue the procedure. The next step is to withdraw the closure dilator and the guidewire while holding the closure sheath 262 in place.

The closure sheath 262 is sized to slidably receive the vascular closure device 250 therein. The distal ends of the closure sheath 262 and the carrier tube 252 have a tapered shape so that the tip will align with the lengthwise axis of the blood vessel 308 when the closure sheath 262 is inserted through the tissue tract 312 at an angle of about 20-45 degrees to the vessel axis.

After the closure sheath 262 is in place, the vascular closure device 250 is introduced into the proximal end of the closure sheath 262. The vascular closure device 250 may be configured to advance until it snaps, locks, or otherwise mates together with the carrier tube 62. In this position, the distal end 264 of the vascular closure device 250 extends out of the distal end of the closure sheath 262 and into the blood vessel 308. It should be noted that the vascular closure device 250 and the closure sheath 262 may be configured so that when they are coupled together, the distal end 264 extends into the blood vessel 308 a predetermined amount.

Figure 4:
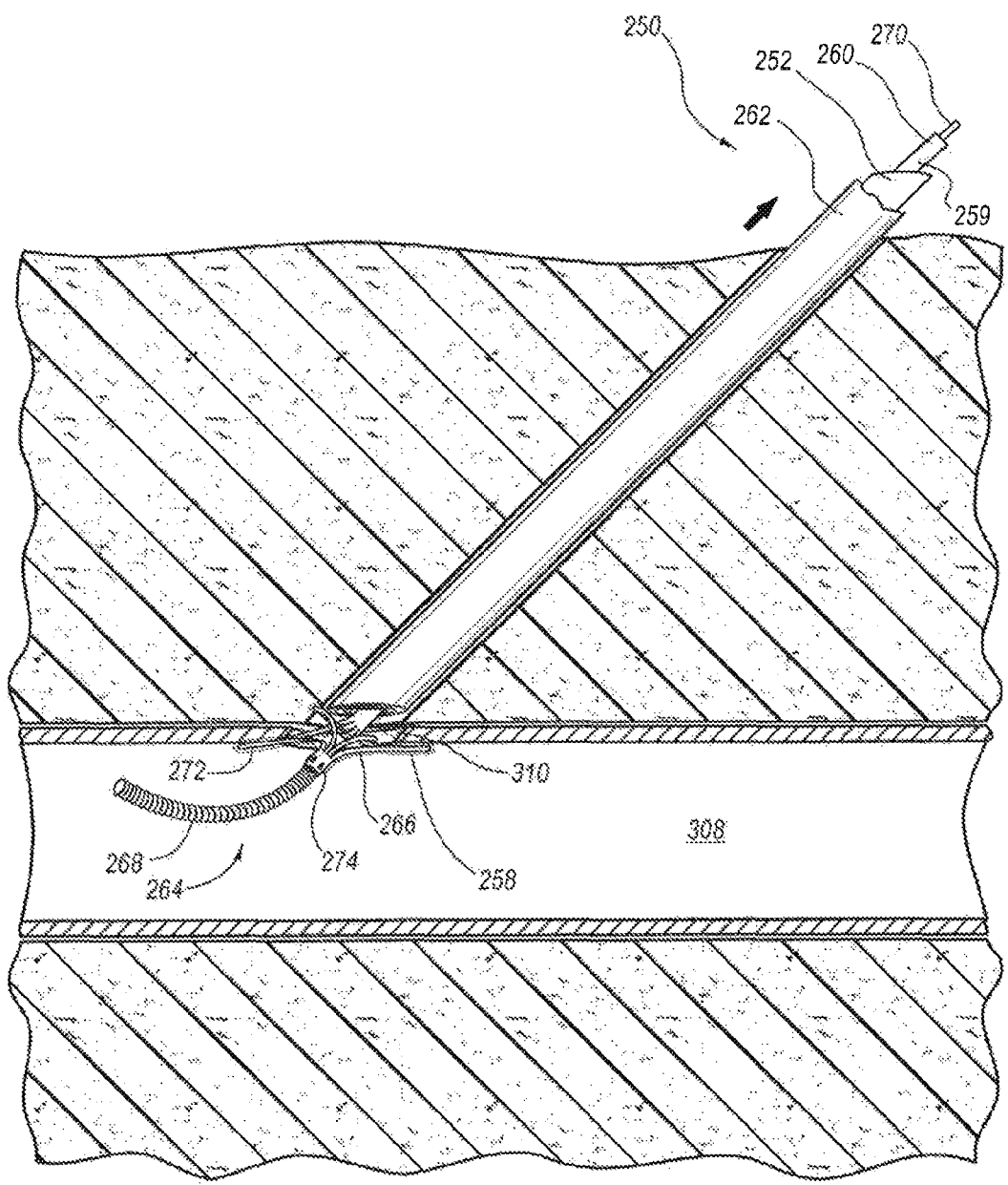
FIG. 4 shows the vascular closure device with the vessel locating member positioned up against the interior wall of the blood vessel.

FIG. 2 shows the vessel locating member 266 in position in the blood vessel 308. The vessel locating member 266 is expanded by pulling the core wire 270 proximally as explained above. FIG. 3 shows the vessel locating member 266 in the expanded configuration. The closure sheath 262 and the vascular closure device 250 are drawn away from the patient until the vessel locating member 266 contacts the vessel wall at the puncture site as shown in FIG. 4.

Figure 5:
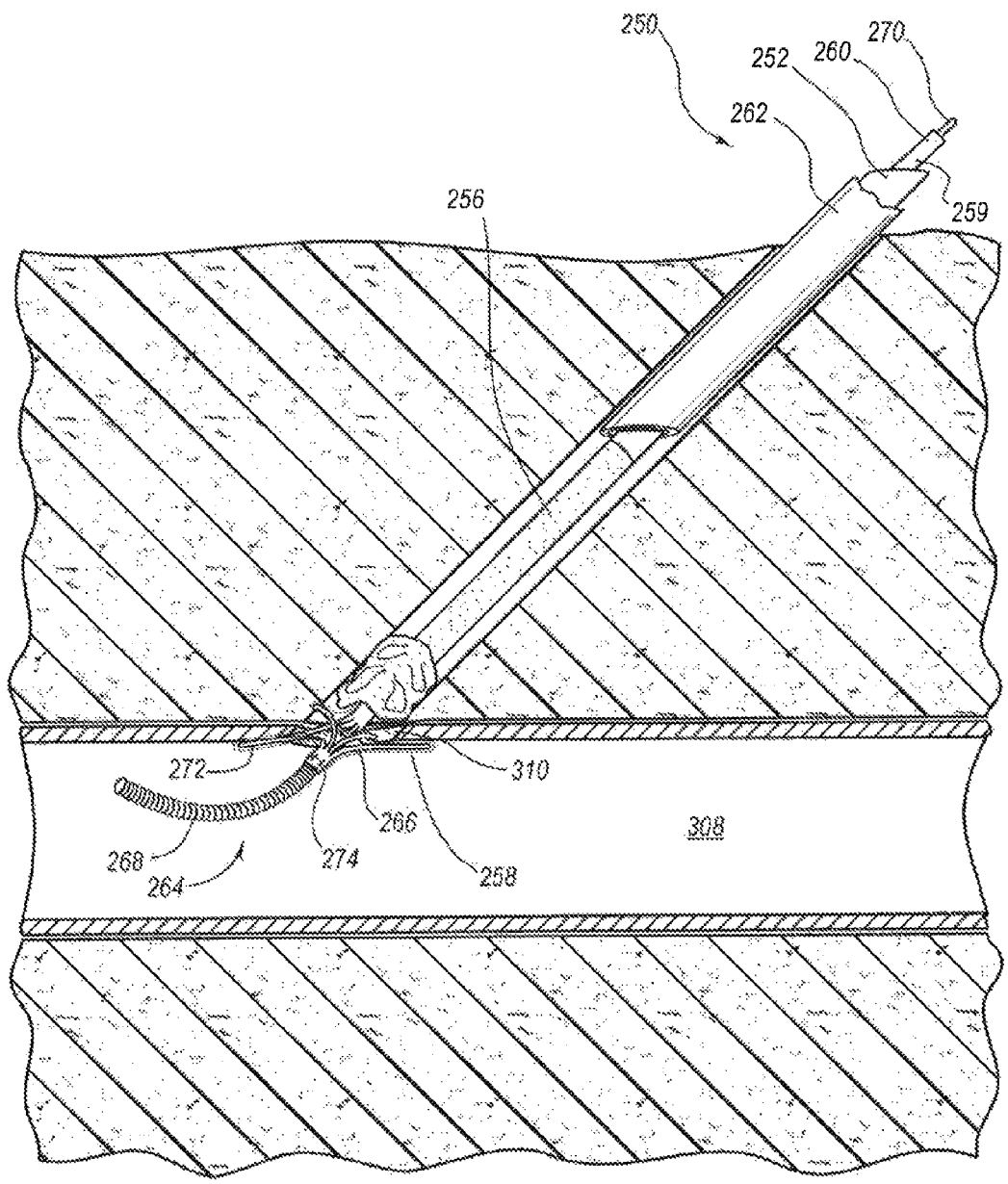
FIG. 5 shows the vascular closure device with the carrier tube and insertion sheath retracted to expose the sealing material to the tissue tract. The sealing material is beginning to change phase and fill in the tissue tract.
Figure 6:
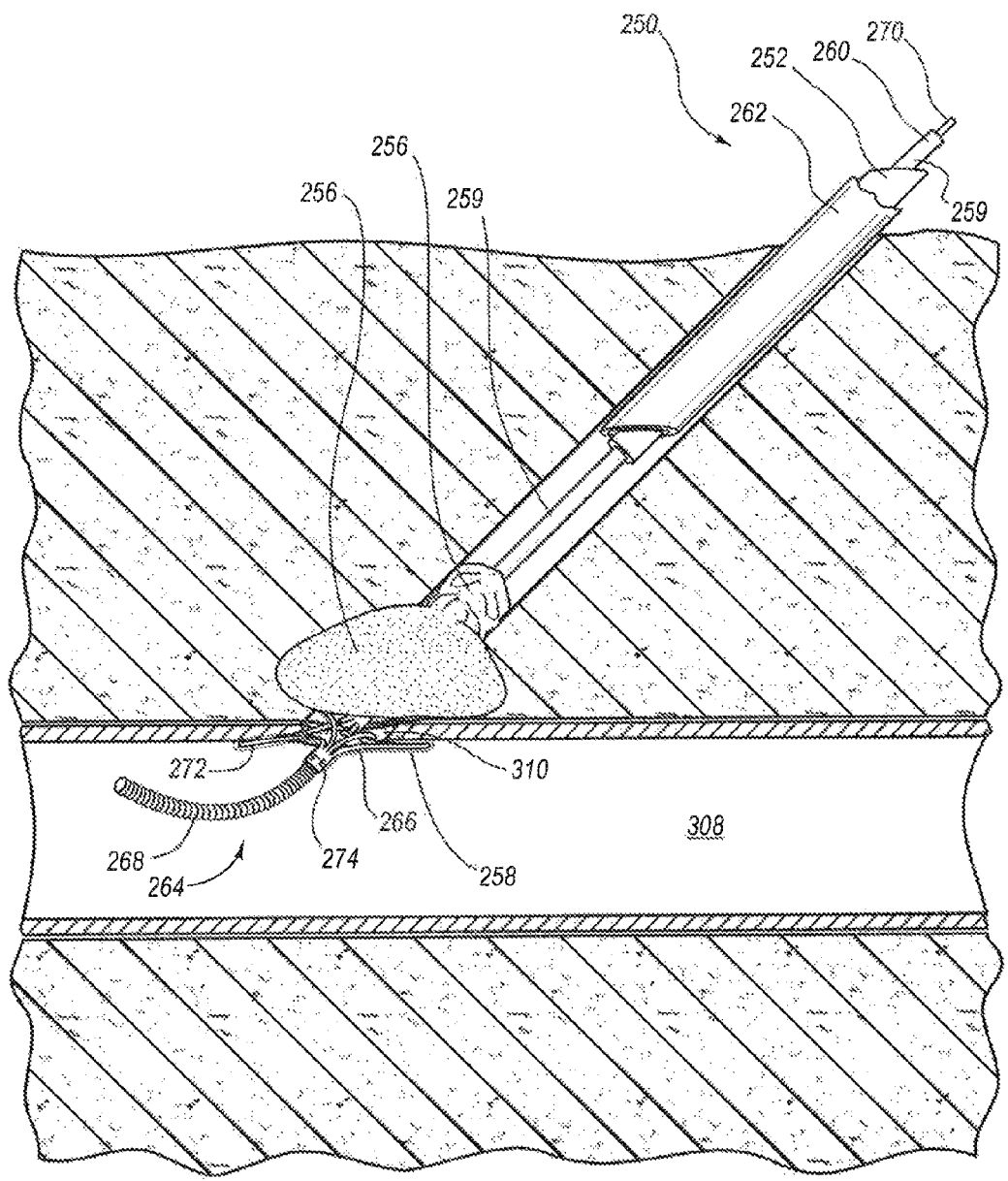
FIG. 6 shows the sealing material as it changes from a liquid/gel to a cubic phase.
Figure 7:
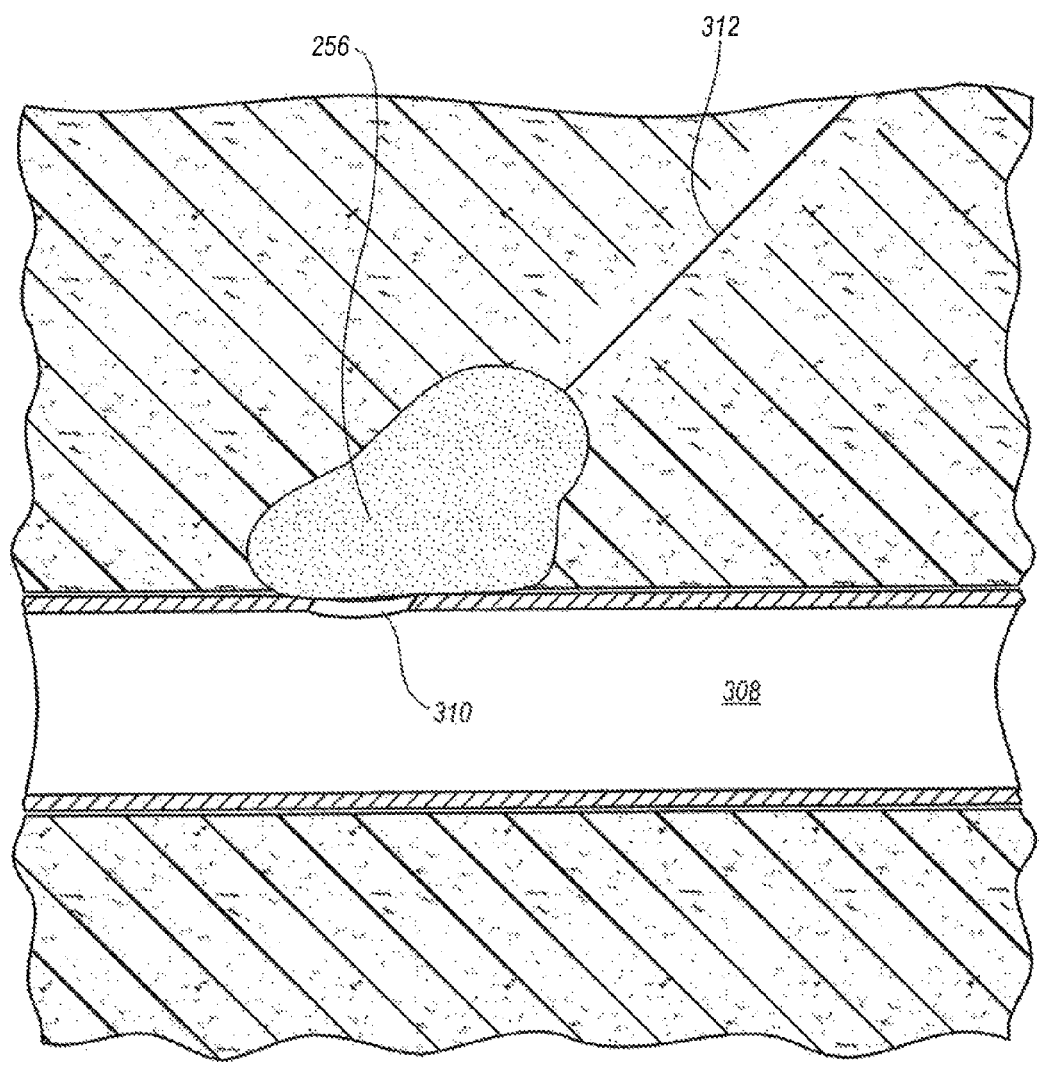
FIG. 7 shows the sealing material deployed adjacent to the hole in the blood vessel after the vascular closure device has been removed.
Figure 8:
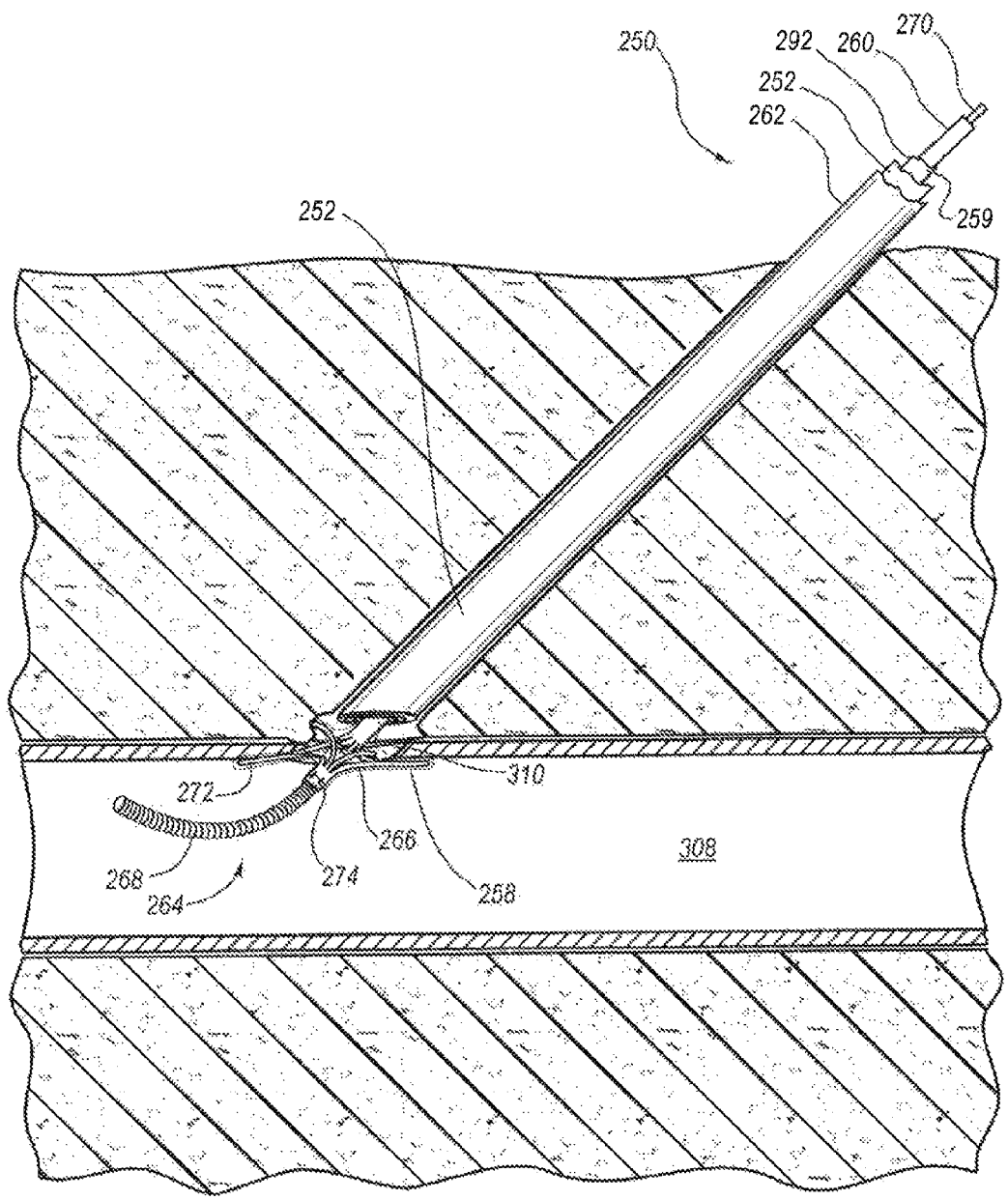
FIGS. 8-11 show another embodiment of the vascular closure device that uses a perforated tube to inject the sealing material into the tissue tract.

Now that the vessel locating member 266 is in position, the closure sheath 262 and the carrier tube 252 are withdrawn to expose the sealing material 256 to the tissue tract 312. The sealing material begins to melt as it is heated by the body and flow down toward the hole 310 to fill all gaps in the puncture tract and between the vessel and subcutaneous connective tissue in the blood vessel 308 as shown in FIG. 5. The membrane 258 is provided over the strut members 272 to help seal the hole 310 and provide temporary hemostasis so that the sealing material 256 does not flow into the blood stream. The sealing material 256 begins to form a cubic phase upon exposure to bodily fluids such as blood and the like. This causes the sealing material 256 to expand and fill in the tissue tract 312 adjacent to the hole 310 in the blood vessel 308 as shown in FIG. 6. It should be appreciated that the vascular closure device 250 may be configured to use a second non-flowable sealing material or anchor along with the sealing material 256. For example, the vascular closure device 250 may be configured to deposit a small collagen plug adjacent to the hole 310 to prevent the sealing material 256 from entering the blood vessel 308.

Now that the sealing material 256 has been deployed and has formed the solid or somewhat firm cubic phase, the next step is to contract the vessel locating member 266 using the core wire 270 as explained above and withdraw the vessel locator assembly 260 and the remainder of the vascular closure device 250 from the tissue tract 312. As the vessel locator assembly 260 passes through the sealing material 256, the sealing material 256 swells or otherwise moves to fill the gap where the vessel locator assembly 260 used to be. The hole in the blood vessel 308 is now sealed by clotting action and the sealing material 256 positioned in the tissue tract 312.

The method of using the vascular closure device 250 shown in FIGS. 8-11 is similar to the method of using the vascular closure device 250 shown in FIGS. 2-7. However, instead of passively allowing the sealing material 256 to melt and fill the tissue tract 312, the user can inject any desired amount of sealing material 256 into the tissue tract 312 through the perforated tube 292. This allows for additional sealing material 256 to be deployed. Also, the user may inject sealing material 256 through the perforated tube 292 as the perforated tube 292 is being withdrawn so that the sealing material fills up the entire tissue tract 312.

It should be appreciated that the embodiments disclosed have many components and the methods described have many steps for operation and use. It is anticipated that the number of components and steps could be altered considerably without departing from the broad scope of what is described herein.

Illustrative Embodiments

Reference is made in the following to a number of illustrative embodiments of the subject matter described herein. The following embodiments illustrate only a few selected embodiments that may include the various features, characteristics, and advantages of the subject matter as presently described. Accordingly, the following embodiments should not be considered as being comprehensive of all of the possible embodiments. Also, features and characteristics of one embodiment may and should be interpreted to equally apply to other embodiments or be used in combination with any number of other features from the various embodiments to provide further additional embodiments, which may describe subject matter having a scope that varies (e.g., broader, etc.) from the particular embodiments explained below. Accordingly, any combination of any of the subject matter described herein is contemplated.

According to one embodiment, a vascular closure device comprises: a vessel locating member configured to be inserted through a hole in a blood vessel to locate a wall of the blood vessel that is adjacent to the hole; and sealing material configured to be deployed adjacent to the hole and outside of the blood vessel; wherein the sealing material is configured to undergo a phase change when deployed to close the hole in the blood vessel. The sealing material may comprise a monoglyceride including a fatty acid group having 12 to 22 carbon atoms. The sealing material may have a melting point that is no more than 37° C. The sealing material may have a melting point of about 27° C. to 37° C.

The sealing material may have a melting point of about 30° C. to 37° C. The sealing material may have a melting point of about 34° C. to 37° C. The sealing material may change to a cubic phase when deployed to close the hole in the blood vessel. The vascular closure device may be configured to be inserted into a tissue tract that leads to the hole in the blood vessel, and wherein the sealing material may be configured to be deployed by retracting a carrier tube to expose the sealing material to the tissue tract. The vascular closure device may be configured to be inserted into a tissue tract that leads to the hole in the blood vessel, and wherein the vascular closure device may be configured so that the sealing material flows out of the vascular closure device in a direction that is not parallel to the tissue tract. The vessel locating member may move between an expanded configuration to allow the vessel locating member to contact an interior surface of the wall of the blood vessel and a contracted configuration to allow the vessel locating member to pass through the hole in the blood vessel. The vessel locating member may be oriented at an oblique angle relative to a lengthwise axis of the vascular closure device. The vessel locating member may be oriented about 20° to 45° from a lengthwise axis of the vascular closure device. The vessel locating member may include a tube having a wall with a plurality of cuts in it, the wall of the tube being configured to expand where the plurality of cuts are located when the tube is compressed. The vessel locating member may include a balloon. The vessel locating member may include a plurality of structural support members covered by a resilient material. The vascular closure device may comprise an indicator that signals when the vessel locating member is positioned adjacent to the wall of the blood vessel.

According to another embodiment, a method of closing a hole in a blood vessel comprises: locating a wall of the blood vessel adjacent to the hole; and deploying sealing material in a tissue tract to close the hole in the blood vessel, the sealing material being deployed a predetermined distance from the wall; wherein the sealing material undergoes a phase change upon being deployed in the tissue tract. The sealing material may comprise a monoglyceride including a fatty acid group having 12 to 22 carbon atoms. The sealing material may have a melting point that is no more than 37° C. The sealing material may have a melting point of about 27° C. to 37° C. The sealing material may have a melting point of about 30° C. to 37° C. The sealing material may have a melting point of about 34° C. to 37° C. The sealing material may change to a cubic phase when deployed to close the hole in the blood vessel. Deploying the sealing material may include removing a covering to expose the sealing material to the tissue tract. Deploying the sealing material may include forcing the sealing material from a vascular closure device in a direction that is not parallel to the tissue tract. Locating the wall of the blood vessel may include inserting a vessel locating member through the hole in the blood vessel, expanding the vessel locating member, and moving the vessel locating member into contact with the wall of the blood vessel. The vessel locating member may be oriented at least substantially parallel to the wall of the blood vessel shortly before contacting the wall. Locating the wall of the blood vessel may be accomplished using a vessel locating member that includes a tube having a wall with a plurality of cuts in it, the wall of the tube being configured to expand where the plurality of cuts are located when the tube is compressed. Locating the wall of the blood vessel may be accomplished using a vessel locating member that includes a balloon. An indicator may signal when the location of the wall has been found.

According to another embodiment, a vascular closure device comprises: a vessel locating member configured to be inserted through a hole in a blood vessel to locate a wall of the blood vessel that is adjacent to the hole; and sealing material configured to be deployed adjacent to the hole and outside of the blood vessel; wherein the sealing material comprises a monoglyceride including a fatty acid group having 12 to 22 carbon atoms. The sealing material may have a melting point that is no more than 37° C. The sealing material may have a melting point of about 27° C. to 37° C. The sealing material may have a melting point of about 30° C. to 37° C. The sealing material may have a melting point of about 34° C. to 37° C. The sealing material may change to a cubic phase when deployed to close the hole in the blood vessel. The vascular closure device may be configured to be inserted into a tissue tract that leads to the hole in the blood vessel, and wherein the sealing material may be configured to be deployed by retracting a carrier tube to expose the sealing material to the tissue tract. The vascular closure device may be configured to be inserted into a tissue tract that leads to the hole in the blood vessel, and wherein the vascular closure device may be configured so that the sealing material flows out of the vascular closure device in a direction that is not parallel to the tissue tract. The vessel locating member may move between an expanded configuration to allow the vessel locating member to contact an interior surface of the wall of the blood vessel and a contracted configuration to allow the vessel locating member to pass through the hole in the blood vessel. The vessel locating member may be oriented at an oblique angle relative to a lengthwise axis of the vascular closure device. The vessel locating member may be oriented about 20° to 45° from a lengthwise axis of the vascular closure device. The vessel locating member may include a tube having a wall with a plurality of cuts in it, the wall of the tube being configured to expand where the plurality of cuts are located when the tube is compressed. The vessel locating member may include a balloon. The vessel locating member may include a plurality of structural support members covered by a resilient material. The vascular closure device may comprise an indicator that signals when the vessel locating member is positioned adjacent to the wall of the blood vessel.

According to another embodiment, a method of closing a hole in a blood vessel comprises: locating a wall of the blood vessel adjacent to the hole; and deploying sealing material in a tissue tract to close the hole in the blood vessel, the sealing material being deployed a predetermined distance from the wall; wherein the sealing material comprises a monoglyceride including a fatty acid group having 12 to 22 carbon atoms. The sealing material may have a melting point that is no more than 37° C. The sealing material may have a melting point of about 27° C. to 37° C. The sealing material may have a melting point of about 30° C. to 37° C. The sealing material may have a melting point of about 34° C. to 37° C. The sealing material may change to a cubic phase when deployed to close the hole in the blood vessel. Deploying the sealing material may include removing a covering to expose the sealing material to the tissue tract. Deploying the sealing material may include forcing the sealing material from a vascular closure device in a direction that is not parallel to the tissue tract. Locating the wall of the blood vessel may include inserting a vessel locating member through the hole in the blood vessel, expanding the vessel locating member, and moving the vessel locating member into contact with the wall of the blood vessel. The vessel locating member may be oriented at least substantially parallel to the wall of the blood vessel shortly before contacting the wall. Locating the wall of the blood vessel may be accomplished using a vessel locating member that includes a tube having a wall with a plurality of cuts in it, the wall of the tube being configured to expand where the plurality of cuts are located when the tube is compressed. Locating the wall of the blood vessel is accomplished using a vessel locating member that includes a balloon. An indicator may signal when the location of the wall has been found.

According to another embodiment, a vascular closure device comprises: sealing material configured to flow out of the vascular closure device and into a tissue tract to close a hole in a blood vessel; wherein the vascular closure device is configured to be inserted into the tissue tract; and wherein the vascular closure device is configured so that the sealing material flows out of the vascular closure device in a direction that is not parallel to the tissue tract. The vascular closure device may be configured to be inserted into a tissue tract that leads to the hole in the blood vessel, and wherein the vascular closure device may be configured so that the sealing material flows out of the vascular closure device in a direction that is at least substantially perpendicular to the tissue tract. The vascular closure device may comprise a perforated tube configured to dispense the sealing material from the vascular closure device, the perforated tube having a distal end that is blocked to prevent the sealing material from flowing out of the perforated tube in a direction that is parallel to the tissue tract. The perforated tube may include a plurality of holes which are of different sizes to control the amount of sealing material dispensed at different points along the length of the perforated tube. The size of the plurality of holes may increase nearer the distal end of the perforated tube. The sealing material may be configured to undergo a phase change when deployed in the tissue tract. The sealing material may change to a cubic phase when deployed in the tissue tract. The sealing arterial may comprise a monoglyceride including a fatty acid group having 12 to 22 carbon atoms. The sealing material may have a melting point that is no more than 37° C. The sealing material may have a melting point of about 27° C. to 37° C. The sealing material may have a melting point of about 30° C. to 37° C. The sealing material may have a melting point of about 34° C. to 37° C.

According to another embodiment, a method of closing a hole in a blood vessel comprises: deploying sealing material in a tissue tract to close the hole in the blood vessel, the sealing material being deployed from a vascular closure device so that the sealing material flows out of the vascular closure device in a direction that is not parallel to the tissue tract. The sealing material may flow out of the vascular closure device in a direction that is at least substantially perpendicular to the tissue tract. The sealing material may flow through a perforated tube and out into the tissue tract. The perforated tube may include a plurality of holes which are of different sizes to control the amount of sealing material dispensed at different points along the length of the perforated tube. The size of the plurality of holes may increase nearer the distal end of the perforated tube. The sealing material may flow through a perforated tube and out into the tissue tract, wherein the perforated tube has a distal end that is blocked to prevent the sealing material from flowing out of the perforated tube in a direction that is parallel to the tissue tract. The sealing material may be configured to undergo a phase change when deployed in the tissue tract. The sealing material may change to a cubic phase when deployed in the tissue tract. The sealing material may comprise a monoglyceride including a fatty acid group having 12 to 22 carbon atoms. The sealing material may have a melting point that is no more than 37° C. The sealing material may have a melting point of about 27° C. to 37° C. The sealing material may have a melting point of about 30° C. to 37° C. The sealing material may have a melting point of about 34° C. to 37° C.

According to another embodiment, a vascular closure device comprises: a carrier tube; and sealing material positioned in the carrier tube, the sealing material being configured to be deployed in a tissue tract to close a hole in a blood vessel; wherein the vascular closure device is configured to deploy the sealing material in the tissue tract by retracting the carrier tube to expose the sealing material to the tissue tract; and wherein the sealing material is configured to flow into the tissue tract when exposed to the tissue tract. The vascular closure device may comprise a stopper positioned between the carrier tube and the sealing material to prevent the sealing material from moving proximally when the carrier tube is retracted. The sealing material may comprise a monoglyceride including a fatty acid group having 12 to 22 carbon atoms. The sealing material may have a melting point that is no more than 37° C. The sealing material may have a melting point of about 27° C. to 37° C. The sealing material may have a melting point of about 30° C. to 37° C. The sealing material may have a melting point of about 34° C. to 37° C. The sealing material may be configured to undergo a phase change when deployed in the tissue tract. The sealing material may change to a cubic phase when deployed to close the hole in the blood vessel. The vascular closure device may be configured so that the sealing material flows out of the vascular closure device in a direction that is not parallel to the tissue tract. The vascular closure device may comprise a vessel locating member configured to be inserted through the hole in the blood vessel to locate a wall of the blood vessel that is adjacent to the hole.

According to another embodiment, a method of closing a hole in a blood vessel comprises: inserting a vascular closure device into a tissue tract, the vascular closure device including sealing material positioned in a carrier tube; and retracting the carrier tube to expose the sealing material to the tissue tract; wherein the sealing material flows into the tissue tract when the carrier tube is retracted. The vascular closure device may comprise a stopper positioned between the carrier tube and the sealing material to prevent the sealing material from moving proximally when the carrier tube is retracted. The sealing material may comprise a monoglyceride including a fatty acid group having 12 to 22 carbon atoms. The sealing material may have a melting point that is no more than 37° C. The sealing material may have a melting point of about 27° C. to 37° C. The sealing material may have a melting point of about 30° C. to 37° C. The sealing material may have a melting point of about 34° C. to 37° C. The sealing material may be configured to undergo a phase change when deployed in the tissue tract. The sealing material may change to a cubic phase when deployed to close the hole in the blood vessel. The vascular closure device may be configured so that the sealing material flows out of the vascular closure device in a direction that is not parallel to the tissue tract. The method may comprise a vessel locating member configured to be inserted through the hole in the blood vessel to locate a wall of the blood vessel that is adjacent to the hole.

According to another embodiment, a vascular closure device comprises: a vessel locating member configured to locate a wall of a blood vessel that is adjacent to a hole in the blood vessel; wherein the vessel locating member includes a plurality of structural support members covered by a resilient material; and wherein the vessel locating member moves between an expanded configuration to allow the vessel locating member to contact the interior surface of the wall of the blood vessel and a contracted configuration to allow the vessel locating member to pass through the hole in the blood vessel. The vessel locating member may include a tube having a wall with a plurality of cuts in it that form the structural support members, the wall of the tube may be configured to expand where the structural support members are located when the tube is compressed. The vessel locating member may be formed by a nitinol tube. The resilient material may include isoprene. The vascular closure device may comprise sealing material configured to be deployed adjacent to the hole and outside of the blood vessel.

According to another embodiment, a method of closing a hole in a blood vessel comprises: inserting a vessel locating member through the hole in the blood vessel, the vessel locating member including a plurality of structural support members covered by a resilient material; expanding the vessel locating member; moving the vessel locating member into contact with the wall of the blood vessel. The vessel locating member may include a tube having a wall with a plurality of cuts in it that form the structural support members, the wall of the tube may be configured to expand where the structural support members are located when the tube is compressed. The vessel locating member may be formed by a nitinol tube. The resilient material may include isoprene. The method may comprise deploying sealing material adjacent to the hole and outside of the blood vessel.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

As used herein, spatial or directional terms, such as "left," "right," "front," "back," and the like, relate to the subject matter as it is shown in the drawing FIGS. However, it is to be understood that the subject matter described herein may assume various alternative orientations and, accordingly, such terms are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9974, and so forth).

What is claimed is:

1. A method of closing a hole in a blood vessel comprising:
   locating a wall of the blood vessel adjacent to the hole; and
   deploying sealing material in a tissue tract to close the hole in the blood vessel, the sealing material being deployed a predetermined distance from the wall;
   wherein the sealing material comprises a monoglyceride including a fatty acid group having 12 to 22 carbon atoms.

2. The method of claim 1 wherein the sealing material has a melting point of about 27° C. to 37° C.

3. The method of claim 1 wherein the sealing material undergoes a phase change when deployed in the tissue tract.

4. The method of claim 1 wherein deploying the sealing material includes removing a covering to expose the sealing material to the tissue tract.

5. The method of claim 1 wherein deploying the sealing material includes forcing the sealing material out of a vascular closure device in a direction that is not parallel to the tissue tract.

6. The method of claim 1 wherein locating the wall of the blood vessel includes inserting a vessel locating member through the hole in the blood vessel, expanding the vessel locating member, and moving the vessel locating member into contact with the wall of the blood vessel.

* * * * *